US007732550B2

(12) United States Patent
Ohnishi et al.

(10) Patent No.: US 7,732,550 B2
(45) Date of Patent: *Jun. 8, 2010

(54) STIMULI-RESPONSIVE POLYMER UTILIZING KETO-ENOL TAUTOMERIZATION AND STIMULI-RESPONSIVE SEPARATING MATERIAL AND CHEMICAL-RELEASING CAPSULE COMPRISING THE SAME

(75) Inventors: Noriyuki Ohnishi, Tsukuba (JP); Kazumi Aoshima, Tsukuba (JP); Kazunori Kataoka, Tokyo (JP); Katsuhiko Ueno, Tsukuba (JP)

(73) Assignees: Agency of Industrial Science & Technology MITI, Osaka (JP); Chisso Corporation, Osaka (JP)

( * ) Notice: Subject to any disclaimer, the term of this patent is extended or adjusted under 35 U.S.C. 154(b) by 623 days.

This patent is subject to a terminal disclaimer.

(21) Appl. No.: 10/869,870

(22) Filed: Jun. 18, 2004

(65) Prior Publication Data

US 2004/0223947 A1 Nov. 11, 2004

Related U.S. Application Data

(62) Division of application No. 10/178,474, filed on Jun. 25, 2002, now Pat. No. 6,852,819, which is a division of application No. 09/207,203, filed on Dec. 8, 1998, now abandoned.

(30) Foreign Application Priority Data

| Dec. 9, 1997 | (JP) | 9-354004 |
| Dec. 19, 1997 | (JP) | 9-354003 |
| Mar. 13, 1998 | (JP) | 10-80581 |
| Mar. 13, 1998 | (JP) | 10-80582 |
| Mar. 13, 1998 | (JP) | 10-80583 |
| Sep. 14, 1998 | (JP) | 10-276403 |

(51) Int. Cl.
*C08F 226/02* (2006.01)
*C08F 20/54* (2006.01)
*C08F 236/02* (2006.01)

(52) U.S. Cl. .............. 526/303.1; 526/307.1; 526/307.2; 526/307.3

(58) Field of Classification Search .............. 526/303.1, 526/307.1, 307.2, 307.3
See application file for complete search history.

(56) References Cited

U.S. PATENT DOCUMENTS

| 2,719,138 | A | * | 9/1955 | Hagemeyer, Jr. et al. .... 525/264 |
| 4,157,323 | A | | 6/1979 | Yen et al. |
| 4,206,094 | A | | 6/1980 | Yen et al. |
| 4,438,239 | A | | 3/1984 | Rembaum et al. |
| 4,571,418 | A | | 2/1986 | Younes |
| 4,780,409 | A | | 10/1988 | Monji et al. |
| 4,935,413 | A | | 6/1990 | Urano et al. |
| 5,284,766 | A | | 2/1994 | Okano et al. |
| 5,354,495 | A | * | 10/1994 | Urano et al. ........... 252/182.18 |
| 5,428,101 | A | | 6/1995 | Urano et al. |
| 5,462,867 | A | * | 10/1995 | Azad et al. .................. 435/181 |
| 5,869,183 | A | * | 2/1999 | Oka et al. .................... 428/398 |
| 5,998,588 | A | | 12/1999 | Hoffman et al. |
| 6,018,033 | A | | 1/2000 | Chen et al. |
| 6,077,908 | A | | 6/2000 | Yahiro |
| 6,852,819 | B2 | * | 2/2005 | Ohnishi et al. ........... 526/303.1 |
| 6,858,694 | B2 | * | 2/2005 | Ohnishi et al. ........... 526/303.1 |

FOREIGN PATENT DOCUMENTS

| BE | 625613 | 6/1969 |
| EP | 0 140 273 | 5/1985 |
| GB | 2 042 528 | 9/1980 |
| JP | 56-22704 | 3/1981 |
| JP | 56-26803 | 3/1981 |
| JP | 61-275260 | 12/1986 |
| JP | 63-46207 | 2/1988 |
| JP | 3-163179 | 7/1991 |
| JP | 7-136505 | 5/1995 |
| JP | 11-255831 | 9/1999 |
| JP | 11-255839 | 9/1999 |
| JP | 3985077 | 7/2007 |
| WO | 97/26288 | 7/1997 |

OTHER PUBLICATIONS

Ohnishi, Database WPI, Section Ch, Week 199530, Derwent Publications Ltd., London, GB, AN 1995-227588, XP002188699 (Abstract of JP 07 136505 (1995).*

Onishi Masato, Database WPI, Section Ch, Week 199530, Derwent Publications Ltd., London, GB, AN 1995-227588, XP002188699 (Abstract of JP 07 136505 (1995).*

T. Aoki et al., "*Molecular Recognition of Bases of Nucleic Acid by a Uracil Group-Containing Polymer Which Form Hydrogen Bonded Polymer Complex*", Polymer Preprints, Japan (English Version), vol. 46, Nos. 6-14 (1997).

K. Nakamura et al., "*Temperature-Responsive Polymeric Hydrogels Derived from 6-(Acryloyloxymethyl)uracil*", Sophia Polymer, pp. 29-30 (1994).

Takashi Aoki et al., *Temperature-Responsive Interpenetrating Polymer Networks Constructed with Poly(acrylic acid) and Poly(N,N-dimethylacrylamide)*, Macromolecules, vol. 27, pp. 947-952 (1994).

Hiroki Katono et al., "*Drug Release OFF Behavior and Deswelling Kinetics of Thermo-Responsive IPNs Composed of Poly(acrylamide-co-butyl methacrylate) and Poly(acrylic acid)*", Polymer Journal, vol. 23, No. 10, pp. 1179-1189 (1991).

(Continued)

*Primary Examiner*—William K Cheung
(74) *Attorney, Agent, or Firm*—Wenderoth, Lind & Ponack, L.L.P.

(57) ABSTRACT

A stimuli-responsive polymer derivative utilizing keto-enol tautomerization. Also disclosed are a simple process for producing an N-acyl(meth)acrylamide derivative which can be used as a monomer for the stimuli-responsive polymer, a process for the production of an intermediate thereof, and an intermediate thus produced.

1 Claim, No Drawings

OTHER PUBLICATIONS

Hiroki Katono et al., "*Thermo-responsive swelling and drug release switching of interpenetrating polymer networks composed of poly(acrylamide-co-butyl methacrylate) and poly(acrylic acid)*", Journal of Controlled Release, vol. 16, pp. 215-228 (1991).

Peter Köberle et al., "*Interactions of a zwitterionic polysoap and its cationic analog with inorganic salts*", Makromol. Chem. Rapid Commun., vol. 12, pp. 427-433 (1991).

Erich E. Kathmann et al., "*Water-Soluble Copolymers. 68. Polyelectrolytes of N-Vinylformamide with Sodium 3-Acrylamido-3-methylbutanoate. Sodium 2-Acrylamido-2-methylpropanesulfonate, and Sodium Acrylate: Solution Behavior*", Macromolecules, vol. 29, pp. 5273-5278 (1996).

T.L. Bowersock et al., "*The potential use of poly(methacrylic acid) hydrogels for oral administration of drugs and vaccines to ruminants*", Journal of Controlled Release, vol. 31, pp. 245-254 (1994).

Database WPI, Section Ch, Week 199530, Derwent Publications Ltd., London, GB, AN 1995-227588, XP002188699 (Abstract of JP 07 136505 (1995).

* cited by examiner

US 7,732,550 B2

STIMULI-RESPONSIVE POLYMER UTILIZING KETO-ENOL TAUTOMERIZATION AND STIMULI-RESPONSIVE SEPARATING MATERIAL AND CHEMICAL-RELEASING CAPSULE COMPRISING THE SAME

This application is a divisional application of Ser. No. 10/178,474, filed Jun. 25, 2002, (now U.S. Pat. No. 6,852,819), which is a divisional application of Ser. No. 09/207,203, filed Dec. 8, 1998, now abandoned.

FIELD OF THE INVENTION

The present invention relates to an excellent stimuli-responsive polymer derivative which can be used for drug delivery system (DDS), chemovalve, various separating agents, catheter, artificial muscle, etc.

BACKGROUND OF THE INVENTION

In recent years, stimuli-responsive polymers have been widely used for drug delivery system (DDS), various separating agents, catheter, artificial muscle, chemovalve, etc. and thus have been of growing importance. For example, JP-A-8-103653 (The term "JP-A" as used herein means an "unexamined published Japanese patent application") discloses a polymer which changes in its higher order structure to swell or shrink in an aqueous solution by the action of heat, light or by a change in pH or potential as a stimuli-responsive polymer. Specifically, acrylamide or methacrylamide derivatives such as poly-N-isopropylacrylamide, N,N-diethylacrylamide and N-isopropylmethacrylamide, and vinylethers such as vinyl methyl ether are disclosed as a polymer having an upper critical solution temperature (UCST) or a lower critical solution temperature (LCST) with respect to water, which swells or shrinks in response to a temperature change.

Although these known polymers which swell or shrink in response to a temperature change are described as having an upper critical solution temperature (UCST) or a lower critical solution temperature (LCST), they all have, in fact, a lower critical solution temperature (LCST). In other words, at a temperature of not lower than the lower critical solution temperature, these polymers reversibly undergo agglomeration of polymers that renders themselves insoluble in water. On the contrary, at a temperature of not higher than the lower critical solution temperature, these polymers can be dissolved in water. For example, poly-N-isopropylacrylamide (PNIPAM), which is applied to DDS, etc. at present, has a lower critical solution temperature of 32° C. in an aqueous solution. When this polymer is allowed to gel, it reversibly undergoes swelling and shrinkage depending on the temperature developed by heat.

A polymer having a lower critical solution temperature (LSCT) shrinks at a predetermined temperature or higher and thus is disadvantageous in that it can be hardly adjusted so as to meet the demand for shrinkage at low temperature (preferably not higher than the body temperature) in the application to DDS, separating agent, etc.

However, all these known thermo-responsive polymers such as poly-N-isopropylacrylamide are stimuli-responsive polymers having a lower critical solution temperature (LCST) which respond only to thermal stimulation. Thus, these thermo-responsive polymers can neither switch a lower critical solution temperature to an upper critical solution temperature (UCST) nor have, in a single compound, both functions of causing their reversible dissolution and precipitation depending on the hydrogen ion concentration, when they respond to heat.

On the other hand, as the polymer which changes in its higher order structure by a pH change there is known a polyacrylic acid or polymethacrylic acid. However, these compounds contain carboxylic acid, which has electric charge, and thus are disadvantageous in that a separating agent comprising such a polymer adsorbs compounds other than desired compounds (non-specific adsorption) and thus cannot provide efficient separation and purification.

If a composite stimuli-responsive polymer which can switch between a lower critical solution temperature (LCST) and an upper critical solution temperature (UCST) or have, in a single compound, both functions of causing its reversible dissolution and precipitation depending on the hydrogen ion concentration can be obtained, the above described adjustment can be easily conducted. The appearance of such a polymer has been desired particularly in an art requiring fine adjustment because such a thermo-responsive polymer can be more widely used.

Further, if used as a separating agent for protein inert to heat, etc., the conventional polymer agglomerates when heated, causing denaturation of protein.

Moreover, if the polymer is used as DDS (e.g., chemical-releasing capsule) by encapsulating a chemical in its gel, it is necessary that the affected part be cooled to allow the gel to swell and release the chemical upon releasing. However, it is practically easy to raise, rather than cool, the temperature of the affected part.

Further, if a thermo-responsive polymer is used as DDS, it needs to exhibit an upper critical solution temperature (UCST) in physiological saline. In this respect, an interpenetration polymer network (IPNa) of polyacrylic acid and polyacryloyl glycinamide is known as a thermo-responsive polymer which exhibits an upper critical solution temperature (UCST) in an aqueous solution (Makromol. Chem., Rapid Commun. 13, 557-581 (1992)). However, this polymer does not exhibit any upper critical solution temperature (UCST) in physiological saline.

Therefore, the appearance of a thermo-responsive polymer which agglomerates when heated in an aqueous solution and exhibits an upper critical solution temperature (UCST) even in physiological saline has been desired.

SUMMARY OF THE INVENTION

An object of the present invention is to provide solution to the above described problems.

A first object of the present invention is to provide a stimuli-responsive polymer which exhibits an upper critical solution temperature (UCST) or a stimuli-responsive polymer which undergoes reversible dissolution and precipitation depending on the hydrogen ion concentration or an addition of a solvent.

A second object of the present invention is to provide a thermo-responsive polymer which exhibits both a lower critical solution temperature (LCST) and an upper critical solution temperature (UCST).

A third object of the present invention is to provide a composite stimuli-responsive polymer which can switch between a lower critical solution temperature (LCST) and an upper critical solution temperature (UCST) or can have, in a single compound, both functions of causing its reversible dissolution and precipitation depending on the hydrogen ion concentration.

A fourth object of the present invention is to provide a thermo-responsive polymer which agglomerates when heated in an aqueous solution and exhibits an upper critical solution temperature (UCST) even in physiological saline.

Further, the present invention also concerns a simple process for producing an N-acyl(meth)acrylamide derivative which can be used as a monomer for the stimuli-responsive polymer, a process for the production of an intermediate thereof, and an intermediate thus produced.

A first aspect of the present invention concerns the following polymer derivatives:

1-1) A stimuli-responsive polymer derivative having an upper critical solution temperature utilizing keto-enol tautomerization.

1-2) A stimuli-responsive polymer derivative utilizing keto-enol tautomerization which undergoes phase transition by a change in hydrogen ion concentration or by an addition of an organic solvent.

1-3) The stimuli-responsive polymer derivative according to the above 1-1) or 1-2), which comprises as a polymerizable component a monomer represented by the following general formula (1):

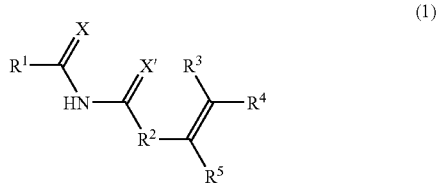

wherein $R^1$ represents a hydrogen atom or a $C_{1-10}$ straight-chain, branched or cyclic alky, alkoxyl, alkylamino, aryl or heterocyclic group which may be halogenated; $R^2$ represents a single bond or a $C_{1-4}$ straight-chain or branched alkylene group which may be halogenated; $R^3$, $R^4$ and $R^5$ each independently represents a hydrogen atom or methyl group; and X and X' each independently represents an oxygen atom, sulfur atom, selenium atom or tellurium atom.

1-4) The stimuli-responsive polymer derivative according to the above 1-1) or 1-2), which comprises as copolymerizable components a hydrophilic or hydrophobic monomer and a monomer represented by general formula (1).

1-5) The stimuli-responsive polymer derivative according to the above 1-3), which comprises as a polymerizable component a monomer represented by the following general formula (7):

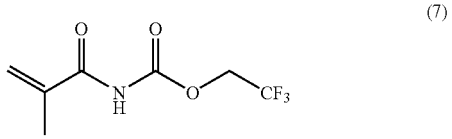

1-6) A stimuli-responsive separating agent comprising a stimuli-responsive polymer derivative according to any one of the above 1-1) to 1-5).

The invention paid attention to strong hydrogen bonding properties represented by peptide bond and reversible keto-enol tautomerization. On the supposition that a thermo-responsive polymer having an upper critical solution temperature (UCST) can be obtained using keto-enol switching as shown in the following reaction formula A, the present invention has been worked out.

Reaction formula A

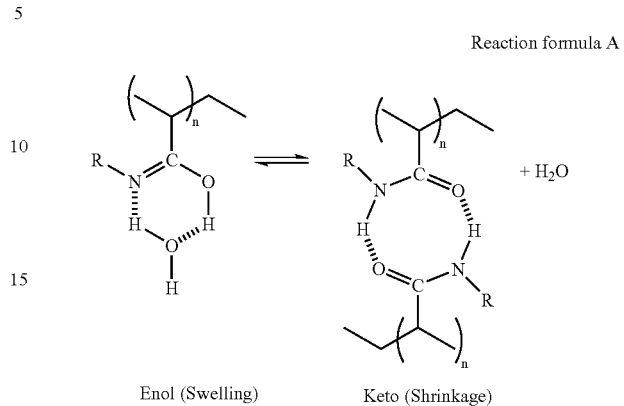

Enol (Swelling)  Keto (Shrinkage)

In other words, the chemical reaction was designed using a computerized method for the calculation of molecular orbital such that enolation occurs at a high temperature to effect hydration and conversion to keto form occurs at a low temperature to effect agglomeration by hydrogen bond. As a result, it was found that the above described design allows the appearance of an upper critical solution temperature (UCST). More particularly, it is preferred to synthesize a compound in which the site having a peptide bond is thermodynamically stable in its keto form.

Further, the above described theory gives a finding that the utilization of keto-enol tautomerization makes it possible to make the above described keto-enol switching (reversible conversion between keto form and enol form) effectively not only by a thermal change but also by a change in hydrogen ion concentration or an addition of an organic solvent, i.e., to obtain a stimuli-responsive polymer which reversibly repeats swelling and shrinkage in accordance with a change in hydrogen ion concentration or an addition of an organic solvent without raising or lowering the temperature.

The stimuli-responsive polymer derivative of the present aspect of the present invention can be effectively applied to the separation, fixing, calibration and control of various substances. In particular, the stimuli-responsive polymer derivative exhibits an upper critical solution temperature (UCST), i.e., agglomerates when the temperature lowers or reversibly repeats swelling and shrinkage in accordance with a change in hydrogen ion concentration or an addition of an organic solvent without raising or lowering the temperature. Accordingly, it is particularly useful for the separation, purification, fixing, calibration and control of substances which are desirably not to be in a high temperature atmosphere (protein such as biological product, enzyme and antibody).

A second aspect of the present invention concerns a copolymer derivative comprising a monomer component having a lower critical solution temperature (LCST) and a monomer component having an upper critical solution temperature (UCST).

As the monomer component having a lower critical solution temperature (LCST), a monomer represented by any one of the following general formulae (2) to (5) can be used:

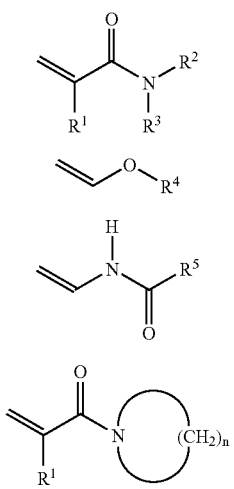

(2)

(3)

(4)

(5)

wherein $R^1$ represents a hydrogen atom or a methyl group; $R^2$ and $R^3$ each independently represents a hydrogen atom or a $C_{1-10}$ straight-chain, branched or cyclic alkyl, alkoxyl, alkylamino, aryl or heterocyclic group which may be halogenated; $R^4$ represents a $C_{1-10}$ straight-chain, branched or cyclic alkyl or alkylakoxyl group which may be halogenated; $R^6$ represents a $C_{1-10}$ straight-chain, branched or cyclic alkyl, alkoxyl, alkylamino, aryl or heterocyclic group which may be halogenated; and n represents an integer of 4 or 5.

As the monomer component having an upper critical solution temperature (UCST), a monomer represented by the above described general formula (1) can be preferably used.

The stimuli-responsive polymer derivative of the present invention may further comprise as a third component a hydrophilic or hydrophobic copolymerizable monomer incorporated therein. The transition point of the stimuli-responsive polymer derivative can be controlled by the incorporation.

It can be presumed that the monomer component represented by the above described general formula (1) exhibits strong hydrogen bonding properties represented by peptide bond and a reversible keto-enol tautomerization and has an upper critical solution temperature (UCST) developed by keto-enol switching as shown in the following reaction formula A:

Reaction formula A

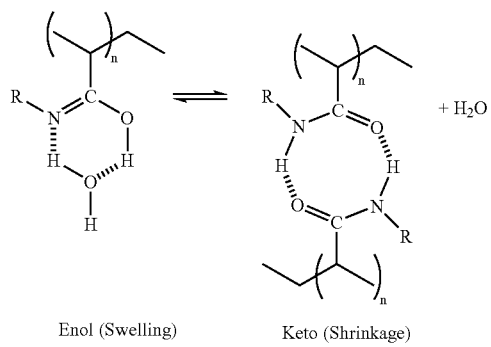

Enol (Swelling)            Keto (Shrinkage)

In other words, the chemical reaction was designed using a computerized method for the calculation of molecular orbital such that enolation occurs at a high temperature to effect hydration and conversion to keto form occurs at a low temperature to effect agglomeration by hydrogen bond. As a result, it was found that the above described design allows the appearance of an upper critical solution temperature (UCST). More particularly, it is preferred to synthesize a compound in which the site having a peptide bond is thermodynamically stable in its keto form.

The thermo-responsive copolymer derivative of the present aspect of the present invention can be effectively applied to the separation, fixing, calibration and control of various substances. In particular, the thermo-responsive copolymer derivative of the present aspect of the present invention has both an upper critical solution temperature (UCST) and a lower critical solution temperature (LCST). Accordingly, it can be effectively used for the separation, purification, fixing, calibration or control of substances the working temperature of which can be hardly predetermined (protein such as biological product, enzyme and antibody). Alternatively, it can be effectively used for chemovalve.

A third aspect of the present invention concerns a composite stimuli-responsive polymer derivative having a lower critical solution temperature (LCST) comprising at least one monomer component represented by the following general formula (6):

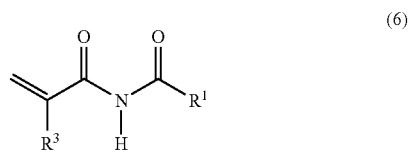

(6)

wherein $R^5$ represents a hydrogen atom or a methyl group; and $R^1$ represents a hydrogen atom or a $C_{1-10}$ straight-chain, branched or cyclic alkyl, alkoxyl, alkylamino, aryl or heterocyclic group which may be halogenated. The compounds of general formula (6) corresponds to compounds of general formula (1) wherein $R^2$ represents a single bond, $R^3$ and $R^4$ each represents a hydrogen atom, and X and X' each represents an oxygen atom.

The above described polymer derivative acts as a thermo-responsive polymer which exhibits a lower critical solution temperature (LCST) in an aqueous solution. The lower critical solution temperature (LCST) can be reversibly changed by the hydrogen ion concentration. In other words, the above described polymer derivative shows a composite stimulation response, that is, individually responds to heat and pH when stimulated by pH.

Further, when put in an aqueous solution having a small amount of an organic solvent added thereto, this thermo-responsive polymer loses the lower critical solution temperature (LCST), which has appeared so far, but exhibits an upper critical solution temperature (UCST). In other words, when stimulated by an organic solvent added, this thermo-responsive polymer undergoes conversion of lower critical solution temperature to upper critical solution temperature.

It is particularly preferred that the stimuli-responsive polymer derivative of the present aspect of the present invention be a copolymer derivative comprising as a copolymerizable component at least one monomer component which is hydrophilic or hydrophobic with respect to the monomer component represented by general formula (6).

The term "monomer component which is hydrophilic or hydrophobic with respect to the monomer component represented by general formula (6)" as used herein is intended to mean, if the monomer of general formula (6) is hydrophobic, a monomer component which is more hydrophilic than the hydrophobic monomer component of general formula (6), and if the monomer of general formula (6) is hydrophilic, a monomer component which is more hydrophobic than the hydrophilic monomer component represented by general formula (6). The hydrophilic or hydrophobic monomer may be a monomer component represented by general formula (6) so far as it is hydrophilic or hydrophobic with respect to the one monomer component represented by general formula (6). In this case, the hydrophilic or hydrophobic monomer contains two or more monomer components represented by general formula (6).

Accordingly, a preferred embodiment of the present aspect of the present invention is a copolymer further comprising at least one monomer component which is hydrophilic or hydrophobic with respect to one monomer component represented by general formula (6) (including a monomer component represented by general formula (6)).

The content of the above described hydrophilic or hydrophobic monomer is preferably from 1 to 70% by weight, more preferably from 3 to 50% by weight based on the total weight of the polymer. When the content of the above described hydrophilic or hydrophobic monomer falls within the above defined range, the above described properties of the present aspect of the present invention can be exerted particularly effectively.

The thermo-responsive polymer derivative of the present aspect of the present invention can be effectively applied to the separation, fixing, calibration or control of various substances. In particular, the thermo-responsive polymer derivative of the present aspect of the present invention is a composite stimuli-responsive polymer which has both an upper critical solution temperature (UCST) and a lower critical solution temperature (LCST) within various temperature ranges and responds also to hydrogen ion concentration. Accordingly, it can be effectively used for the separation, purification, fixing, calibration or control of substances the working temperature of which can be hardly predetermined (protein such as biological product, enzyme and antibody). Alternatively, it can be effectively used for chemovalve.

A fourth aspect of the present invention concerns a thermo-responsive polymer derivative having an upper critical solution temperature (UCST) in an aqueous solution, which comprises at least one monomer component represented by the following general formula (6) and at least one monomer component selected from acrylamide and methacrylamide:

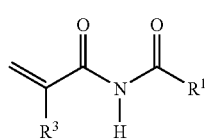

(6)

wherein $R^5$ represents a hydrogen atom or methyl group; and $R^1$ represents a hydrogen atom or a $C_{1-10}$ straight-chain, branched or cyclic alkyl, alkoxyl, alkylamino, aryl or heterocyclic group which may be halogenated.

The thermo-responsive polymer derivative of the present aspect of the present invention is a copolymer derivative comprising at least one monomer component represented by general formula (6) and at least one monomer component selected from acrylamide and methacrylamide as copolymerizable components.

In the present aspect of the present invention, the charged proportion of the monomer represented by general formula (6) is preferably from 0.1 to 100% by weight, more preferably from 1 to 30% by weight, particularly from 5 to 15% by weight based on the weight of acrylamide and/or methacrylamide.

The thermo-responsive polymer derivative of the present aspect of the present invention may further comprise at least one hydrophilic or hydrophobic monomer component which is hydrophilic or hydrophobic with respect to monomer component represented by general formula (6) (excluding acrylamide and methacrylamide) incorporated therein as a copolymerizable component as necessary. The term "monomer component which is hydrophilic or hydrophobic with respect to the monomer component represented by general formula (6)" as used herein is intended to mean, if the monomer of general formula (6) is hydrophobic, a monomer component which is more hydrophilic than the hydrophobic monomer component of general formula (6), and if the monomer of general formula (6) is hydrophilic, a monomer component which is more hydrophobic than the hydrophilic monomer component represented by general formula (6). The hydrophilic or hydrophobic monomer may be a monomer component represented by general formula (6) so far as it is hydrophilic or hydrophobic with respect to the one monomer component represented by general formula (6). In this case, the hydrophilic or hydrophobic monomer contains two or more monomer components represented by general formula (6).

The charged proportion of the above described hydrophilic or hydrophobic monomer is preferably from 1 to 70% by weight, more preferably from 3 to 50% by weight based on the total weight of the monomer component represented by general formula (6) and acrylamide and/or methacrylamide.

The thermo-responsive polymer derivative of the present invention exhibits an upper critical solution temperature (UCST) in an aqueous solution, particularly physiological saline, and thus can be effectively applied to the separation, fixing, calibration or control of various substances. Accordingly, it can be effectively used for the separation, purification, fixing, calibration or control of substances the working temperature of which can be hardly predetermined (protein such as biological product, enzyme and antibody). Alternatively, it can be effectively used for chemovalve, drug delivery system (DSS), etc.

DETAILED DESCRIPTION OF THE INVENTION

The present invention will be further described hereinafter.

In accordance with the first aspect of the present invention, as mentioned above, by properly making a molecular design using keto-enol tautomerization, a stimuli-responsive polymer derivative having an upper critical solution temperature (UCST) or a stimuli-responsive polymer derivative which undergoes phase transition in accordance with a change in hydrogen ion concentration or an addition of an organic solvent can be easily obtained.

For example, a polymer derivative containing a substituent component represented by the following general formula (8) may be preferably used:

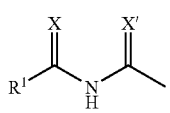

(8)

wherein R¹, X and X' are the same as those defined in general formula (1), respectively. The preferred ranges thereof are also the same as those described below with reference to general formula (1).

In the polymer derivative containing a substituent component represented by general formula (8) (hereinafter described with reference to the case where X and X' each represents an oxygen atom for the simplification of description), the amide bonding site shows reversible switch between keto form and enol form as shown in the following reaction formula B in accordance with an application of heat, a change in the hydrogen ion concentration, or with an addition of an organic solvent.

Reaction formula B

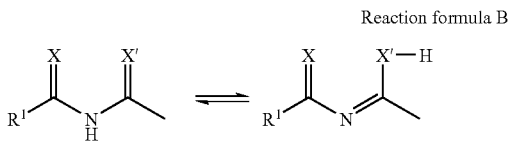

Further, the present inventors found that a polymer derivative containing a monomer represented by the above described general formula (1) as a polymer component is particularly effective for efficient reversible keto-enol conversion.

In general, a compound having an amide bond itself agglomerates due to strong hydrogen bonding in an aqueous solution. A polyamide which takes a keto form in an aqueous solution is insoluble in water. However, it can be presumed that this keto form is converted to an enol form due to heat or a change in hydrogen ion concentration to lose its self-agglomeration effect, giving a water-soluble compound.

The monomer represented by general formula (1) is described in more detail below.

In general formula (1), $R^1$ preferably represents a $C_{1-8}$ straight-chain, branched or cyclic alkyl, alkoxyl, alkylamino or phenyl group, more preferably methyl, ethyl, propyl, isopropyl, phenyl, methoxy, propoxyl, isopropoxyl, methylamino or ethylamino group, particularly methyl, ethoxy or methylamino group. These groups may be substituted by a halogen atom such as fluorine, bromine, chlorine and iodine. Particularly preferred substituents are fluorine atom and chlorine atom.

$R^2$ preferably represents a single bond or $C_{1-2}$ straight-chain or branched alkylene group or halogenated alkylene group, particularly a single bond. Preferred examples of substituents on the alkylene group include fluorine atom and chlorine atom.

X and X' each is preferably an oxygen atom or sulfur atom.

Examples of the monomer represented by general formula (1) include N-acetylacrylamide, N-fluoroacetylacrylamide, N-propionylacrylamide, N-butanoylacrylamide, N-pentanoylacrylamide, N-hexanoylacrylamide, N-isobutanoylacrylamide, N-benzoylacrylamide, N-(3-fluorobenzoyl)acrylamide, N-(2,3-difluorobenzoyl)acrylamide, N-pyridylcarbonylacrylamide, N-pyrimidylcarbonylacrylamide, N-acetylmethacrylamide, N-fluoroacetylmethacrylamide, N-propionylmethacrylamide, N-butanoylmethacrylamide, N-pentanoylmethacrylamide, N-hexanoylmethacrylamide, N-isobutanoylmethacrylamide, N-benzoylmethacrylamide, N-(3-fluorobenzoyl)methacrylamide, N-(2,3-difluorobenzoyl)methacrylamide, N-pyridylcarbonylmethacrylamide, N-pyrimidylcarbonylmethacrylamide, N-acroyl-N'-methylurea, N-acroyl-N'-ethylurea, N-acroyl-N'-fluoromethylurea, N-acroyl-N'-difluoromethylurea, N-acroyl-N'-trifluoromethylurea, N-methacroyl-N'-methylurea, N-methacroyl-N'-ethylurea, N-methacroyl-N'-fluoromethylurea, N-methacroyl-N'-difluoromethylurea, N-methacroyl-N'-trifluoromethylurea, methyl N-acroylcarbamate, ethyl N-acroylcarbamate, n-propyl N-acroylcarbamate, isopropyl N-acroylcarbamate, n-butyl N-acroylcarbamate, isobutyl N-acroylcarbamate, fluoromethyl N-acroylcarbamate, difluoromethyl N-acroylcarbamate, trifluoromethyl N-acroylcarbamate, 2,2,2-trifluoroethyl N-acroylcarbamate, methyl N-methacroylcarbamate, ethyl N-methacroylcarbamate, n-propyl N-methacroylcarbamate, isopropyl N-methacroylcarbamate, n-butyl N-methacroylcarbamate, isobutyl N-methacroylcarbamate, t-butyl N-methacroylcarbamate, fluoromethyl N-methacroylcarbamate, difluoromethyl N-methacroylcarbamate, trifluoromethyl N-methacroylcarbamate, and 2,2,2-trifluoroethyl N-methacroylcarbamate.

Specifically, homopolymerization of a monomer represented by general formula (1) or copolymerization of a monomer represented by general formula (1) with a hydrophilic or hydrophobic monomer makes it possible to obtain thermo-responsive polymers having a UCST within various temperature ranges, pH-responsive polymers which respond to various hydrogen ion concentrations or solvent-responsive polymers which respond to an addition of an organic solvent.

Further, copolymerization of a monomer represented by general formula (1) with a monomer for a thermo-responsive polymer having an LCST makes it possible to obtain a heat- and pH-responsive polymer which exhibits both heat response and pH response.

The thermo-responsive polymer having a UCST preferably exhibits an upper critical solution temperature of from 0 to 50° C., particularly from 0 to 38° C., if it is used as a separating agent.

Further, the switching range of the thermo-responsive polymer (range of phase transition temperature) is preferably as narrow as possible. In accordance with the present invention, a thermo-responsive polymer having a practical switching range of higher than 10° C. can be obtained.

The organic solvent to be used for stimulation is not specifically limited so far as it has some solubility in water. Specific examples of the organic solvent include methanol, ethanol, propanol, isopropanol, acetone, THF, dioxane, acetic acid, propionic acid, ethylene glycol, and propylene glycol. Preferred among these organic solvents are methanol, ethanol, propanol, isopropanol, acetone, and THF. These organic solvents can efficiently accelerate the agglomeration of the stimuli-responsive polymer, though depending on the kind of the stimuli-responsive polymer.

It was also found that the application of stimulation by an organic solvent makes it possible to develop a keto-enol switching type heat response.

Further, the novel stimuli-responsive polymer derivative of the present invention is effective for the separation, fixing, calibration or control of substances which are desirably not to be in a high temperature atmosphere. It can be effectively applied to drug delivery system (DDS), various separating agents, catheter, artificial muscle, etc.

In particular, the stimuli-responsive polymer derivative of the present invention can contain a region having affinity for the target substance and a region showing the above described stimulation response to provide an effective stimuli-responsive separating material.

The stimuli-responsive separating material of the present invention may be in any embodiment normally used in the art. The target substance is not specifically limited. In practice, however, protein (e.g., enzyme, antibody, molecular chaperon, biological product), glycoprotein, nucleic acid, cell, artificial cell, synthetic polymer, etc. may be used.

The separating material of the present invention is a material containing a region having a stimulation response utilizing the above described keto-enol tautomerization and a region having affinity for the target substance. The region having a stimulation response preferably contains a substituent component represented by general formula (8). More particularly, it preferably contains a monomer component represented by general formula (1) as a copolymerizable component.

The region having affinity for the target substance contains a component which can be bonded to or adsorbed by the target substance. More particularly, the polymer derivative of the invention preferably contains a monomer component containing the above described component which can be bonded to or adsorbed by the target substance as a component copolymerizable with the above described monomer component showing a stimulation response. The bonding of the monomer component to the target substance does not necessarily need to be a covalent bond but may be a bond utilizing ion complex or charge-transfer complex or bond utilizing a biochemical affinity.

Furthermore particularly, a protein such as antibody and enzyme, if any, can be bonded to the stimuli-responsive material (region having affinity) by making the use of the reactivity of a functional group such as amino group and carboxyl group which is often contained in such a protein. For example, if an amino group in a protein is used, a carboxyl group may be incorporated in the stimuli-responsive material to produce an amide bond by the following reaction formula:

Condensation agent

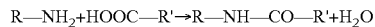

R—NH$_2$+HOOC—R'→R—NH—CO—R'+H$_2$O wherein R represents a protein; and R' represents a stimuli-responsive material A method utilizing an aldehyde group and a method utilizing an epoxy group as mentioned below may be used:

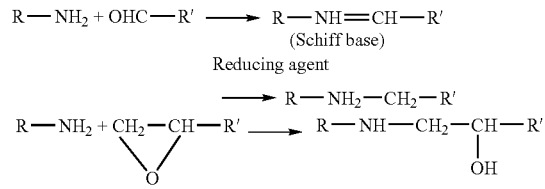

Further, if a carboxyl group in a protein is used, an amino group may be incorporated in the stimuli-responsive material to produce an amide bond by the following reaction formula:

Condensation agent

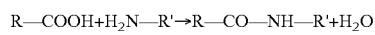

R—COOH+H$_2$N—R'→R—CO—NH—R'+H$_2$O

Further, an antibody may be incorporated in the stimuli-responsive material so that it is bonded to a protein as target substance. This operation is preferably effected in phosphoric acid or trisbuffer having a pH value in the vicinity of neutrality. The salt concentration may be properly predetermined depending on the purpose.

Moreover, a particulate magnetic material may be bonded to the stimuli-responsive material to effect complexing. In this arrangement, a stimuli-responsive material to which the target substance has been bonded or by which the target has been adsorbed can be more efficiently agglomerated by the use of a magnet or the like during separation.

The target substance which has been bonded to or adsorbed by the stimuli-responsive material of the present invention can be easily eluted out by any of (1) raising the salt concentration, (2) changing the pH value (rendering the solution acidic or alkaline), (3) adding an inhibitor, substrate, etc., (4) adding a modifier such as urea and SDS, (5) adding an organic solvent, metal ion, etc. and (6) changing the temperature.

More particularly, the stimuli-responsive separating material of the present invention can be applied to medicine for detecting residual agricultural chemical or diagnostic medicine and can be effectively used for the activation or maintenance of biological reaction by separation of biological products such as microorganisms and product of cell culture or fixing of enzyme or molecular chaperon.

In accordance with the second aspect of the present invention, as mentioned above, a thermo-responsive polymer derivative having both a lower critical solution temperature (LCST) and an upper critical solution temperature (UCST) can be obtained by copolymerizing at least one monomer component having a lower critical solution temperature (LCST) with at least one monomer component having an upper critical solution temperature (UCST).

In the second aspect of the present invention, as the monomer component having a lower critical solution temperature (LCST) there may be preferably used a monomer component represented by any of the above described general formulae (2) to (5).

Particularly preferred embodiments of the various substituents in general formulae (2) to (5) are described below.

$R^1$ preferably is a hydrogen atom or methyl group. $R^2$ and $R^3$ each is preferably a hydrogen atom, methyl group, ethyl group, propyl group, isopropyl group, n-butyl group, isobutyl group or tert-butyl group. $R^4$ is preferably a methyl group. $R^5$ is preferably a methyl group, ethyl group, propyl group, isopropyl group, n-butyl group, isobutyl group or tert-butyl group.

Specific examples of the monomer component represented by general formula (2) include N-methylacrylamide, N-ethylacrylamide, N-cyclopropylacrylamide, N-isopropylacrylamide, N-n-propylacrylamide, N-tert-butylacrylamide, N-sec-butylacrylamide, N-n-butylacrylamide, N-methylmethacrylamide, N-ethylmethacrylamide, N-cyclopropylmethacrylamide, N-isopropylmethacrylamide, N-n-propylmethacrylamide, N-tert-butylmethacrylamide, N-sec-butylmethacrylamide, N-n-butylmethacrylamide, N,N-dimethylacrylamide, N,N-diethylacrylamide, N,N-dimethylmethacrylamide, N,N-diethylmethacrylamide, N-methyl-N-ethylacrylamide, N-methyl-N-isopropylacrylamide, N-methyl-N-n-propylacrylamide, N-methyl-N-ethylmethacrylamide, N-methyl-N-isopropylmethacrylamide, N-methyl-N-n-propylmethacrylamide, N,N-diisopropylacrylamide, N,N-di-n-propylacrylamide, N,N-diisopropylmethacrylamide, and N,N-di-n-propylmethacrylamide.

Specific examples of the monomer component represented by general formula (3) include methyl vinyl ether, and methoxy ethyl vinyl ether.

Specific examples of the monomer component represented by general formula (4) include N-vinylacetamide, N-vinylpropionamide, N-vinylbutyrylamide, and N-vinyl isobutyrylamide.

Specific examples of the monomer component represented by general formula (5) include N-acetylacrylamide, N-fluoroacetylacrylamide, N-propionylacrylamide, N-butanoylacrylamide, N-pentanoylacrylamide, N-hexanoylacrylamide, N-isobutanoylacrylamide, N-benzoylacrylamide, N-(3-fluorobenzoyl)acrylamide, N-(2,3-difluorobenzoyl)acrylamide, N-pyridylcarbonylacrylamide, N-pyrimidylcarbonylacrylamide, N-acetylmethacrylamide, N-fluoroacetylmethacrylamide, N-propionylmethacrylamide, N-butanoylmethacrylamide, N-pentanoylmethacrylamide, N-hexanoylmethacrylamide, N-isobutanoylmethacrylamide, N-benzoylmethacrylamide, N-(3-fluorobenzoyl)methacrylamide, N-(2,3-difluorobenzoyl)methacrylamide, N-pyridylcarbonylmethacrylamide, N-pyrimidylcarbonylmethacrylamide, N-acroyl-N'-methylurea, N-acroyl-N'-ethylurea, N-acroyl-N'-fluoromethylurea, N-acroyl-N'-difluoromethylurea, N-acroyl-N'-trifluoromethylurea, N-methacroyl-N'-methylurea, N-methacroyl-N'-ethylurea, N-methacroyl-N'-fluoromethylurea, N-methacroyl-N'-difluoromethylurea, N-methacroyl-N'-trifluoromethylurea, methyl N-acroylcarbamate, ethyl N-acroylcarbamate, n-butyl N-acroylcarbamate, isopropyl N-acroylcarbamate, n-butyl N-acroylcarbamate, isobutyl N-acroylcarbamate, t-butyl N-acroylcarbamate, fluoromethyl N-acroylcarbamate, difluoromethyl N-acroylcarbamate, trifluoromethyl N-acroylcarbamate, 2,2,2-trifluoroethyl N-acroylcarbamate, methyl N-methacroylcarbamate, ethyl N-methacroylcarbamate, n-butyl N-methacroylcarbamate, isopropyl N-methacroylcarbamate, n-butyl N-methacroylcarbamate, isobutyl N-methacroylcarbamate, t-butyl N-methacroylcarbamate, fluoromethyl N-methacroylcarbamate, difluoromethyl N-methacroylcarbamate, trifluoromethyl N-methacroylcarbamate, and 2,2,2-trifluoroethyl N-methacroylcarbamate.

On the other hand, as the monomer component having an upper critical solution temperature (UCST) there may be preferably used a monomer containing a substituent component represented by general formula (8).

In the second aspect of the present invention, the composition ratio of the monomer component having a lower critical solution temperature (LCST) to the monomer component having an upper critical solution temperature (UCST) is not specifically limited but can be properly predetermined depending on the purpose. In general, the weight ratio of the monomer component having a lower critical solution temperature to the monomer component having an upper critical solution temperature is preferably from 2:1 to 1:5.

The molecular weight of the polymer derivative of the second aspect of the present invention is not specifically limited. The polymer derivative shows little or no dependence of properties such as transition temperature on the molecular weight thereof. The molecular weight of the polymer derivative is normally from about $10^2$ to $10^6$, preferably from about $10^3$ to $10^5$.

Further, in the second aspect of the present invention, the copolymerization of a monomer component having a lower critical solution temperature (LCST) and a monomer component having an upper critical solution temperature (UCST) further with a hydrophilic or hydrophobic monomer makes it possible to obtain thermo-responsive polymers which exhibit a lower critical solution temperature (LCST) and an upper critical solution temperature (UCST) within various temperature ranges.

The hydrophilic or hydrophobic monomer to be used herein is not specifically limited. Various compounds may be used as such. Specific examples of the hydrophilic monomer include acrylamide, allylamine, hydroxylethyl (meth)acrylate, and glycerin mono(meth)acrylate. Specific examples of the hydrophobic monomer include ester (meth)acrylate, vinyl chloride, vinylidene chloride, and styrene.

Further, the switching range (range of transition temperature) is preferably as narrow as possible. In accordance with the second aspect of the present invention, a thermo-responsive polymer having a practical switching range of not higher than 10° C. can be obtained.

Further, the novel stimuli-responsive polymer derivative of the second aspect of the present invention is effective for the separation, fixing, calibration or control of substances which are desirably not to be in a high temperature atmosphere. It can be effectively applied to drug delivery system (DDS), various separating agents, catheter, artificial muscle, chemovalve, etc.

A stimuli-responsive polymer derivative according to the third aspect of the present invention can be obtained, as mentioned above, by polymerizing at least one monomer component represented by general formula (6) or copolymerizing at least one monomer component represented by general formula (6) with at least one monomer component which is hydrophilic or hydrophobic with respect to the monomer component.

The monomer component represented by general formula (6) is described in detail below.

Preferred examples and particularly preferred examples of R' in general formula (6) include those described with reference to $R^1$ in general formula (1). Specific examples of the monomer represented by general formula (6) include those described with reference to general formula (1).

The hydrophilic or hydrophobic monomer to be additionally incorporated as a copolymerizable component in the third aspect of the present invention cannot be unequivocally defined because it is hydrophilic or hydrophobic with respect to one monomer component represented by general formula (6). Besides the monomer of general formula (1), (meth)acrylamide and (meth)acrylic acid may be used as hydrophilic monomers and ester (meth)acrylate, vinyl chloride, vinylidene chloride, and styrene may be used as hydrophobic monomers.

In the third aspect of the present invention, as mentioned above, the incorporation of a monomer component represented by general formula (6) and optionally a monomer component which is hydrophilic or hydrophobic with respect to the monomer component represented by general formula (6) makes it possible to obtain polymer derivatives having various lower critical solution temperatures (LCST). The polymer derivative of the third aspect of the present invention loses its transition point in an acidic or alkaline solution having a predetermined or higher acidity or alkalinity, e.g., aqueous solution of caustic soda having a normality of not less than 0.1 N, though depending on the kind of the monomer component used.

The organic solvent to be added to water to develop an upper critical solution temperature (UCST) in the third aspect of the present invention is not specifically limited so far as it has solubility in water. Specific examples of the organic solvent employable herein include methanol, ethanol, propanol, isopropanol, acetone, THF, dioxane, acetic acid, propionic acid, ethylene glycol, and propylene glycol.

Preferred among these organic solvents are methanol, ethanol, propanol, isopropanol, acetone, and THF. These organic solvents can efficiently accelerate the agglomeration of the stimuli-responsive polymer.

The amount of the organic solvent to be added depends on the kind of the stimuli-responsive polymer. In practice, however, it may be normally from about 5 to 50% by weight so that the lower critical solution temperature (LCST) disappears while a lower critical solution temperature (LCST) appears.

The molecular weight of the polymer derivative of the third aspect of the present invention is not specifically limited. The polymer derivative shows little or no dependence of properties such as transition temperature on the molecular weight thereof. In practice, however, the weight-average molecular weight of the polymer derivative is normally from about $10^2$ to $10^6$, preferably from about $10^3$ to $10^5$.

In the third aspect of the present invention, the switching range of the thermo-responsive polymer (range of phase transition temperature) is preferably as narrow as possible. In accordance with the third aspect of the present invention, a thermo-responsive polymer having a practical switching range of not higher than 10° C. can be obtained.

The novel stimuli-responsive polymer derivative of the second aspect of the present invention is effective for the separation, fixing, calibration or control of substances which are desirably not to be in a high temperature atmosphere. It can be effectively applied to drug delivery system (DDS), various separating agents, catheter, artificial muscle, chemovalve, etc.

A thermo-responsive polymer derivative according to the fourth aspect of the present invention can be obtained, as described above, by copolymerizing at least one monomer component represented by general formula (6) with at least one monomer component selected from acrylamide and methacrylamide and optionally the above described hydrophilic or hydrophobic monomer component.

Preferred examples and particularly preferred examples of $R^1$ in general formula (6) include those described with reference to $R^1$ in general formula (1).

Specific examples of the monomer represented by general formula (6) include those described with reference to general formula (1), and N-formylacrylamide and N-formylmethacrylamide.

The hydrophilic or hydrophobic monomer to be additionally incorporated as a copolymerizable component in the fourth aspect of the present invention cannot be unequivocally defined because it is hydrophilic or hydrophobic with respect to one monomer component represented by general formula (6). Besides the monomer of general formula (6), acrylamide and methacrylamide, (meth)acrylic acid, etc. may be used as hydrophilic monomers and ester (meth)acrylate, vinyl chloride, vinylidene chloride, and styrene may be used as hydrophobic monomers.

The molecular weight of the polymer derivative of the fourth aspect of the present invention is not specifically limited. The polymer derivative shows little or no dependence of properties such as transition temperature on the molecular weight thereof. In practice, however, the weight-average molecular weight of the polymer derivative is normally from about $10^2$ to $10^6$, preferably from about $10^3$ to $10^5$.

The thermo-responsive polymer having a UCST preferably exhibits an upper critical solution temperature of from 0 to 50° C., particularly from 0 to 38° C., if it is used as a separating agent.

In the fourth aspect of the present invention, the switching range of the thermo-responsive polymer (range of phase transition temperature) is preferably as narrow as possible. In accordance with the fourth aspect of the present invention, a thermo-responsive polymer having a practical switching range of not higher than 10° C. can be obtained.

The novel stimuli-responsive polymer derivative of the fourth aspect of the present invention is effective for the separation, fixing, calibration or control of substances which are desirably not to be in a high temperature atmosphere. It can be effectively applied to drug delivery system (DDS), various separating agents, catheter, artificial muscle, chemovalve, etc.

In particular, the stimuli-responsive polymer derivative of the present invention can contain a region having affinity for the target substance and a region showing the above described stimulation response to provide an effective stimuli-responsive separating material or chemical-releasing capsule. Chemical-releasing capsules are formulations which release a chemical enclosed therein controllably with reversible swelling and shrinkage due to a temperature or pH change. These formulations have been spotlighted as intelligent formulations which can give a chemical in a required amount as necessary.

The stimuli-responsive separating material and chemical-releasing capsule of the present invention may be in any embodiment normally used in the art. The target substance is not specifically limited. In practice, however, protein (e.g., enzyme, antibody, molecular chaperon, biological product), glycoprotein, nucleic acid, cell, artificial cell, synthetic polymer, various chemicals (e.g., carcinostatic such as adriamycin, taxol), etc. may be used.

The separating material and chemical-releasing capsule of the present invention are materials having a region showing the above described stimulation response and a region having affinity for the target substance. The region showing a stimulation response may contain a substituent component represented by general formula (6).

Further, the thermo-responsive polymer of the fourth aspect of the present invention, if incorporated in a chemical-releasing capsule, is preferably provided in the form of a thermo-responsive hydrogel containing at least one monomer component represented by general formula (6), at least one monomer component selected from acrylamide and methacrylamide, and a crosslinking agent as a copolymerizable component which is used as a chemical-releasing capsule.

As the above described crosslinking agent there is preferably used a compound terminated by double bond at both ends thereof. Examples of such a compound include N,N'-methylenebisacrylamide, divinylbenzene, divinylsulfone, diallyl carbinol, divinylether, and 1,5-hexadiene.

A process for simply producing an N-acyl(meth)acrylamide derivative which can be used as a monomer of a stimuli-responsive polymer, a process for producing an intermediate thereof and an intermediate thus produced are described below.

To date, several methods for the synthesis of N-acyl(meth)acrylamide have been developed. However, these synthesis methods leave something to be desired in yield and productivity. These synthesis methods and their problems will be described hereinafter.

The reaction of acrylamide and ketene gas as starting materials represented by the following reaction formula (J. A. C. S., vol. 23, pp. 915-916 (1958)) gives a good yield but requires the use of ketene gas, which is very toxic.

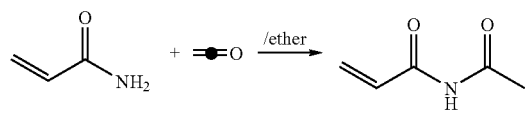

The reaction of acrylamide and an acid anhydride as starting materials represented by the following reaction formula (JP-B-37-9212 (The term "JP-B" as used herein means an "examined Japanese patent publication")) produces Michael adducts besides N-acetylated compounds and thus gives a poor yield.

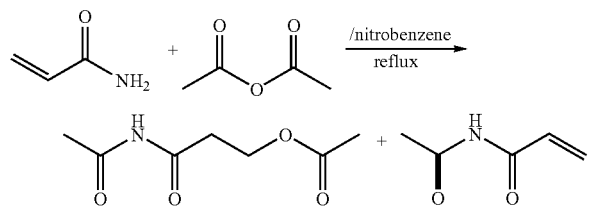

The reaction of acrylamide and an acid chloride represented by the following reaction formula (U.S. Pat. No. 852,460) gives much by-products and hence a poor yield.

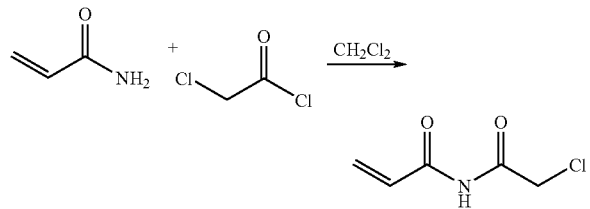

In order to solve the above described problems, a simple production process which gives a good yield has been desired.

As a result of the extensive studies made by the present inventors, simple production processes were found as described below.

That is, an N-acyl(meth)acrylamide derivative can be simply produced by reacting:

an isocyanate represented by general formula (9):

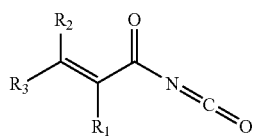

(9)

wherein $R_1$ represents a hydrogen atom or a methyl group; and $R_2$ and $R_3$ each independently represents a hydrogen atom or a $C_{1-10}$ straight-chain or branched alkyl group which may be halogenated; with an organic metal compound represented by the following general formula (10):

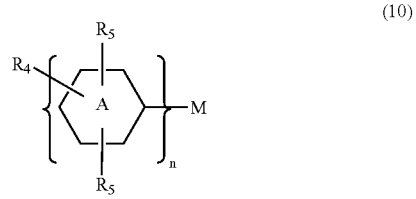

(10)

wherein M represents an alkaline metal or a halogenated alkaline earth metal; the ring A represents a cyclohexane ring, cyclopentane ring, cyclopentadiene ring, pyridine ring, pyrimidine ring or benzene ring; n represents a positive number of from 0 to 4; and $R_4$, $R_5$ and $R_6$ each independently represents a hydrogen atom, a $C_{1-10}$ optionally halogenated straight-chain or branched alkyl group or halogen atom directly connected to the ring A or M, with the proviso that if n is 0, $R_4$ is neither a hydrogen atom nor a halogen atom, to thereby produce an N-acyl(meth)acrylamide derivative represented by general formula (11):

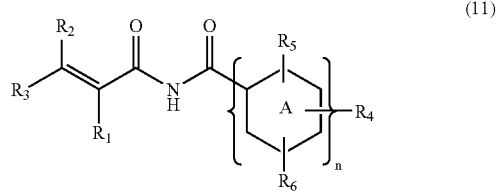

(11)

wherein $R_1$ to $R_6$, the ring A and n are as defined above can be simply produced.

In other words, by using an isocyanate represented by general formula (9) instead of the conventional acrylamide as a starting material and reating it with an organic metal reagent represented by general formula (10), the desired N-acyl(meth)acrylamide derivative can be simply obtained in a high yield.

In the isocyanate represented by general formula (9), $R_1$ to $R_3$ preferably each represents a hydrogen atom or methyl group.

Isocyanates represented by general formula (9) and organic metal compounds represented by general formula (10) are all commercially available or may be easily produced from commercially available compounds by known methods.

The solvent to be used in the above described production process is not specifically limited so far as it has no adverse effects on the reaction. Various solvents may be used so far as they do not react with a nucleophilic reagent. Such a solvent may be selected from aliphatic hydrocarbon solvents such as cyclohexane, hexane and heptane, aromatic hydrocarbon solvents such as benzene and toluene, halogenated hydrocarbon solvents such as 1,2-dichloroethane, chloroform and carbon tetrachloride and ether solvents such as diethyl ether, dioxane and tetrahydrofurane (THF). These solvents may be used singly or in admixture.

The reaction is effected normally at a temperature of from −78° C. to 70° C., preferably from −40° C. to 35° C. The reaction time is not specifically limited. In practice, however, the reaction may be terminated when it ends in accordance with ordinary method. In general, the reaction time ranges from several minutes to 24 hours.

The compound represented by general formula (11) obtained according to the present invention may be effectively used as a monomer component of stimuli-responsive polymer which swells or shrinks due to a temperature or pH change or an addition of a solvent or polymer such as plastic modifier optionally together with other copolymerizable components. Further, analogues of this compound may be used as herbicides (see U.S. Pat. No. 852,460).

SYNTHESIS EXAMPLE 1-1

Synthesis of N-acetyl methacrylamide 10 ml of methacroyl isocyanate was dissolved in 50 ml of THF in a flask. To the solution was then added dropwise 35 ml of a 3 mol/l THF solution of methyl magnesium bromide at a temperature of −20° C. in an atmosphere of nitrogen. After the termination of the dropwise addition, the mixture was then stirred at room temperature for 1 hour. To the mixture were then added 100 ml of a 2 N hydrochloric acid and 100 ml of ethyl acetate sequentially. The resulting organic phase was then washed twice with saturated brine. The solvent was then distilled off under reduced pressure. The residue thus obtained was then recrystallized from ethyl acetate to obtain 5.3 g of a colorless crystal (yield: 48%). NMR analysis gave a strong indication that the product is the desired compound.

COMPARATIVE SYNTHESIS EXAMPLE 1-1

Synthesis of N-acetyl methacrylamide by conventional method 23.7 g of acrylamide and 60 ml of triethylamine were dissolved in 100 ml of dichloromethane in a flask. To the solution was then added dropwise 27.6 g of acetyl chloride at a temperature of −30° C. After the termination of the dropwise addition, the mixture was then stirred at a temperature of 0° C. for 10 hours. Triethylamine hydrochloride thus precipitated was then filtered off. The filtrate was then subjected to distillation under reduced pressure to remove the solvent therefrom. The residue thus obtained was then subjected to column chromatography with ethyl acetate as a developing solvent and silica gel as a filler to obtain 1.5 g of the desired compound (yield: 4%).

SYNTHESIS EXAMPLE 1-2

Synthesis of N-benzoyl methacrylamide 2 ml of methacroyl isocyanate was dissolved in 20 ml of THF in a flask. To the solution was then added dropwise a 3 mol/l THF solution of phenyl lithium at a temperature of −20° C. in an atmosphere of nitrogen. After the termination of the dropwise addition, the mixture was then stirred at room temperature for 1 hour. To the mixture were then added 100 ml of a 2 N hydrochloric acid and 100 ml of ethyl acetate sequentially. The resulting organic phase was then washed twice with saturated brine. The solvent was then distilled off under reduced pressure. The residue thus obtained was then recrystallized from ethyl acetate to obtain 1.3 g of a colorless crystal (yield: 40%). NMR analysis gave a strong indication that the product is the desired compound.

SYNTHESIS EXAMPLE 1-3

Synthesis of Other N-acyl(meth)acrylamide Derivatives

The isocyanates represented by general formula (9) and the organic metal compound represented by general formula (10) set forth in the table below were reacted in the same manner as in Synthesis Example 1-1. As a result, the desired compound (11) was obtained in a yield set forth in the table below.

TABLE 1

| | Compound of general formula (10) | | |
|---|---|---|---|
| Compound of general formula (9) | Phenyl lithium | Ethyl magnesium bromide | Propyl magnesium bromide |
| Acroyl isocyanate | 55% | 45% | 43% |
| Methacroyl isocyanate | 51% | 47% | 44% |

In accordance with the above described production process of the present invention, an N-acyl(meth)acrylamide derivative which can be used as a monomer for a stimuli-responsive polymer or modifier or as a starting material of herbicide can be simply synthesized in a good yield.

Another production process is described below.

That is, an N-acyl(meth)acrylamide derivative can be simply produced by reacting:

an amide represented by the following general formula (12):

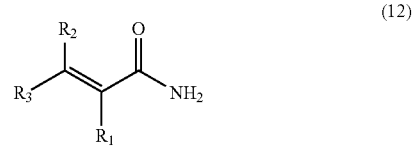

(12)

wherein $R_1$ represents a hydrogen atom or a methyl group; and $R_2$ and $R_3$ each independently represents a hydrogen atom or a $C_{1-10}$ straight-chain or branched alkyl group which may be halogenated; with a compound represented by the following general formula (13):

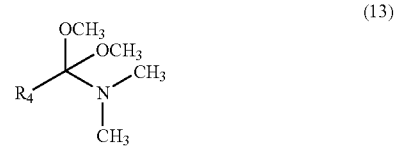

(13)

wherein $R_4$ represents a $C_{1-10}$ straight-chain or branched alkyl group or a $C_{5-6}$ cyclic alkyl, aryl or heterocyclic group, each of which may be halogenated, to thereby produce an enamine compound represented by the following general formula (14):

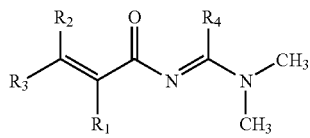

(14)

wherein $R_1$ to $R_4$ are as defined above; and then allowing the enamine compound to undergo hydrolysis under acidic conditions, to thereby produce an N-acyl(meth)acrylamide derivative represented by the following general formula (15):

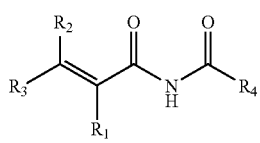

(15)

wherein $R_1$ to $R_4$ are as defined above.

This process of the present invention is characterized by using an acrylamide as a starting material and reacting it with a reagent represented by general formula (13) to produce a novel enamine represented by general formula (14). Further, in accordance with this process of the present invention, the enamine can be hydrolyzed under acidic conditions to simply produce the desired N-acyl(meth)acrylamide in a good yield.

In the acrylamide represented by general formula (12), $R_1$ to $R_3$ each preferably represent a hydrogen atom or a methyl group.

In the reagent represented by general formula (13), $R_4$ preferably represents a methyl group, ethyl group, trifluoromethyl group, cyclohexyl group or phenyl group.

Acrylamides represented by general formula (12) and reagents represented by general formula (13) are all commercially available or may be easily produced from commercially available compounds by known methods.

In the synthesis of an enamine at the first stage, the reaction can proceed without any solvent. However, some solvent is preferably used from the standpoint of operation efficiency and yield. The solvent employable herein is not specifically limited so far as it has no adverse effects on the reaction. Various solvents may be used. Such a solvent may be selected from aliphatic hydrocarbon solvents such as cyclohexane, hexane and heptane, aromatic hydrocarbon solvents such as benzene and toluene, halogenated hydrocarbon solvents such as 1,2-dichloroethane, chloroform and carbon tetrachloride and ether solvents such as diethyl ether, dioxane and tetrahydrofurane (THF). These solvents may be used singly or in admixture.

The first stage of the reaction is effected normally at a temperature of from 0° C. to 200° C., preferably from 40° C. to 80° C. The reaction time for the first stage is not specifically limited. In practice, however, the reaction may be terminated when it ends in accordance with ordinary method. In general, the reaction time ranges from 30 minutes to 24 hours.

The hydrolysis reaction at the second stage can proceed without any solvent. However, some solvent is preferably used from the standpoint of operation efficiency and yield. The solvent employable herein is not specifically limited so far as it has no adverse effects on the reaction. A water-soluble solvent is preferably used. Examples of such a solvent include ether solvents such as dioxane and tetrahydrofurane (THF), alcohols such as methanol, ethanol, propanol and isopropanol and organic acids such as acetic acid and propionic acid. These solvents may be used singly or in admixture.

As the acidic substance to be used in the hydrolysis reaction there may be used any acidic substance such as protonic acid, Lewis acid and organic acid without any restriction so far as it has no adverse effects on the reaction. Examples of such an acidic substance include hydrochloric acid, sulfuric acid, nitric acid, iron chloride, copper chloride, zinc chloride, acetic acid, propionic acid and trifluoroacetic acid. These acidic substances may be used singly or in admixture.

The reaction at the second stage is effected normally at a temperature of from 0° C. to 100° C., preferably from 10° C. to 30° C. The reaction time for the second stage is not specifically limited. In practice, however, the reaction may be terminated when it ends in accordance with ordinary method. In general, the reaction time ranges from 30 minutes to 24 hours.

The compound represented by general formula (15) obtained according to the present invention may be effectively used as a monomer component of stimuli-responsive polymer which swells or shrinks due to a temperature or pH change or an addition of a solvent, or polymer such as plastic modifier optionally together with other copolymerizable components. Further, analogues of this compound may be used as herbicides (see U.S. Pat. No. 852,460).

SYNTHESIS EXAMPLE 2-1

Synthesis of N-acetyl acrylamide 31 g of acrylamide and 80 g of N,N-dimethylacetamide dimethylacetal were dissolved in 200 ml of THF in a flask. The mixture was then stirred at a temperature of 65° C. for 3 hours. The disappearance of the starting materials was then confirmed by gas chromatography. Thereafter, the solvent was distilled off by an evaporator. The initial distillate was distilled off under reduced pressure to obtain 40 g of (N,N-dimethylacetamide)imine in the form of slightly yellowed liquid.

NMR analysis gave a strong indication that the product is the above described imine substance, as follows.

$^1$H-NMR analysis: δ2.25 (multi. 6H), δ3.10 (s. 3H), δ5.64 (multi. 1H), δ6.27 (multi. 2H).

The imine thus obtained was dissolved in a mixture of 200 ml of a 2 N hydrochloric acid and 40 ml of acetic acid, and then stirred at room temperature for 4 hours. The disappearance of the imine as a starting material was then confirmed by gas chromatography. Thereafter, to the solution were added 100 ml of water and 100 ml of ethyl acetate. The resulting organic phase was then washed with an aqueous solution of sodium bicarbonate until it became neutral. The organic phase was then dried over magnesium sulfate. The aqueous phase was collected together, and then extracted with ethyl acetate. The resulting organic phase was washed with an aqueous solution of sodium bicarbonate until it became neutral, and then added to the first batch of organic phase which was then again dried.

The solvent was then distilled off by an evaporator. The residue was then subjected to column chromatography with silica gel produced by Merck and ethyl acetate as a developing solvent to remove unreacted acrylamide therefrom. The fraction thus obtained was concentrated, and then recrystallized twice from ethyl acetate to obtain 20 g of the desired compound having a purity of 99.6% in the form of white crystal (yield: 41%).

NMR analysis gave a strong indication that the product is N-acetyl acrylamide as follows:

$^1$H-NMR analysis: δ2.47 (s. 3H), δ5.89 (tri. 1H), δ6.48 (d. 2H), δ7.27 (s. 1H).

COMPARATIVE SYNTHESIS EXAMPLE 2-1

Synthesis of N-acetyl acrylamide by conventional method 23.7 g of acrylamide and 60 ml of triethylamine were dissolved in 100 ml of dichloromethane in a flask. To the solution was then added dropwise 27.6 g of acetyl chloride at a temperature of −30° C. After the termination of the dropwise addition, the mixture was then stirred at a temperature of 0° C. for 10 hours. Triethylamine hydrochloride thus precipitated was then filtered off. The filtrate was then subjected to distillation under reduced pressure to remove the solvent therefrom. The residue thus obtained was then subjected to column chromatography with ethyl acetate as a developing solvent and silica gel as a filler to obtain 1.5 g of the desired compound (yield: 4%).

SYNTHESIS EXAMPLE 2-2

Synthesis of N-acetyl methacrylamide 33 g of methacrylamide and 80 g of N,N-dimethylacetamide dimethylacetal were dissolved in 200 ml of THF in a flask. The mixture was then stirred at a temperature of 65° C. for 3 hours. The disappearance of the starting materials was then confirmed by gas chromatography. Thereafter, the solvent was distilled off by an evaporator. The initial distillate was distilled off under reduced pressure to obtain 50 g of (N,N-dimethylacetamide)imine substance in the form of slightly yellowed liquid. NMR analysis gave a strong indication that the product is the desired imine.

The imine thus obtained was dissolved in a mixture of 200 ml of a 2 N hydrochloric acid and 40 ml of acetic acid, and then stirred at room temperature for 4 hours. The disappearance of the imine as a starting material was then confirmed by gas chromatography. Thereafter, to the solution were added 100 ml of water and 100 ml of ethyl acetate. The resulting organic phase was then washed with an aqueous solution of sodium bicarbonate until it became neutral. The organic phase was then dried over magnesium sulfate. The aqueous phase was collected together, and then extracted with ethyl acetate. The resulting organic phase was washed with an aqueous solution of sodium bicarbonate until it became neutral, and then added to the first batch of organic phase which was then again dried.

The solvent was then distilled off by an evaporator. The residue was then subjected to column chromatography with silica gel produced by Merck and ethyl acetate as a developing solvent to remove unreacted methacrylamide therefrom. The fraction thus obtained was concentrated, and then recrystallized twice from ethyl acetate to obtain 30 g of the desired compound having a purity of 99.8% in the form of white crystal (yield: 62%).

NMR analysis gave a strong indication that the product is N-acetyl methacrylamide as follows:

$^1$H-NMR analysis: δ2.00 (multi. 3H), δ2.50 (s. 3H), δ5.66 (qur. 1H), δ5.96 (d. 1H), δ9.41 (br. s. 1H).

In accordance with the above described production process of the present invention, an N-acyl(meth)acrylamide derivative which can be used as a monomer for a stimuli-responsive polymer or modifier or as a starting material of herbicide can be simply synthesized via a novel enamine in a high yield.

The present invention described in greater detail with reference to the following Examples and comparative Examples, but the present invention should not be construed as being limited thereto.

EXAMPLE 1-1

Synthesis of N-acetyl (Meth)acrylamide (Scheme a)

Scheme a:

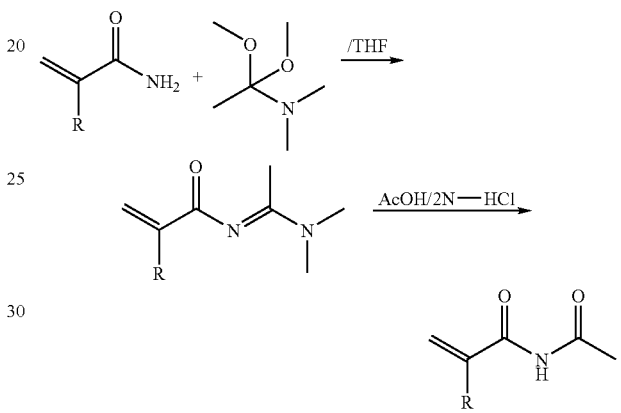

In an atmosphere of nitrogen gas, 30.5 g of acrylamide, 80 g of N,N-dimethylacetamide dimethylacetal and 400 ml of THF were charged in a flask, and then stirred at a temperature of 65° C. for 3 hours. The reaction solution thus obtained was concentrated under reduced pressure. The residue was subjected to simple distillation under a pressure of 1 mmHg to obtain 45 g of an acroylimide. The acroylimide thus obtained was dissolved in 100 ml of a 2 N hydrochloric acid, and then charged into a flask. To the solution was then added 20 ml of acetic acid. The mixture was then stirred at room temperature for 4 hours. The reaction solution was then extracted with ethyl acetate. The resulting organic phase was then concentrated under reduced pressure. The residue was then subjected to column chromatography with ethyl acetate as a solvent. The resulting fraction was then concentrated under reduced pressure. The residue was then recrystallized from ethyl acetate as a solvent to obtain 30 g of a white crystal.

The above described synthesis procedure was followed except that 30.5 g of methacrylamide was used as a starting material. As a result, 32 g of the desired compound was obtained.

NMR analysis gave a strong indication that the product is the desired compound.

EXAMPLE 1-2

Synthesis and physical properties of poly-N-acetyl acrylamide

In an atmosphere of nitrogen gas, 1.0 g of N-acetyl acrylamide and 10 mg of AIBN were dissolved in ethanol, and then charged into a flask where it was then stirred at a temperature of 75° C. for 3 hours. The polymer thus precipitated was withdrawn by filtration, thoroughly washed with ethanol, and then dried at room temperature under reduced pressure to obtain 850 mg of a white solid.

50 g of the polymer thus obtained was heated and dissolved in 5 ml of a 10% ethanol solution, 20% ethanol solution and 30% ethanol solution, respectively, and then allowed to cool. In this manner, these polymer solutions were measured for transparent point upon heating in the form of uniform cloudy liquid. As a result, these polymer solutions showed a transparent point of 38.5° C., 39.4° C. and 41.9° C., respectively. After reaching the transparent point, these polymer solutions were measured for cohesion temperature upon cooling. As a result, these polymer solutions were observed to show USCT at 44.7° C., 45.2° C. and 50.2° C., respectively. These polymer solutions reversibly underwent dissolution and precipitation many times at these temperatures.

The measurement of transition temperature was effected as calculated in terms of visible light transmittance.

The transition temperature range (temperature range required until the transmittance reached from 2% to 100% upon heating or from 98% to 0% upon cooling) was as very narrow as from 2 to 6° C., though depending on the ethanol concentration.

EXAMPLE 1-3

Synthesis and physical properties of poly-N-acetyl methacrylamide

In an atmosphere of nitrogen gas, 1.0 g of N-acetyl methacrylamide and 10 mg of AIBN were dissolved in ethanol, and then charged into a flask where it was then stirred at a temperature of 75° C. for 3 hours. The polymer thus precipitated was withdrawn by filtration, thoroughly washed with ethanol, and then dried at room temperature under reduced pressure to obtain 810 mg of a white solid.

50 mg of the polymer thus obtained was then dissolved in 5 ml of a 1 N aqueous solution of sodium hydroxide. To the solution thus obtained was then added dropwise a 0.1 N hydrochloric acid. As a result, it was confirmed that the polymer thus obtained is a pH-responsive polymer which repeatedly undergoes dissolution at a pH value of not less than 10.3 and precipitation at a pH value of not more than 10.3.

EXAMPLE 1-4

Synthesis and physical properties of N-acetyl methacrylamide and N-isopropyl acrylamide copolymer In an atmosphere of nitrogen gas, 1.0 g of N-acetyl methacrylamide, 1.0 g of N-isopropyl acrylamide and 10 mg of AIBN were dissolved in ethanol, and then charged into a flask where it was then stirred at a temperature of 75° C. for 3 hours. The polymer thus precipitated was withdrawn by filtration, thoroughly washed with ethanol, and then dried at room temperature under reduced pressure to obtain 1.1 g of a white solid.

50 mg of the polymer thus obtained was dissolved in 5 ml of a buffer having pH 1, buffer having pH 5, buffer having pH 7, buffer having pH 10 and buffer having pH 12, respectively. In this manner, these polymer solutions were measured for its LCST. As a result, these polymer solutions showed LCSTs of 52° C., 48° C., 48° C., 35° C. and 32° C., respectively. The transition temperature range (temperature range required until the transmittance reached from 98% to 0%) was as very sharp as from 1.5 to 6° C., though depending on pH.

COMPARATIVE EXAMPLE 1-1

Synthesis and physical properties of poly-N-isopropyl acrylamide (PNIPAM)

In an atmosphere of nitrogen gas, 1.0 g of N-isopropyl acrylamide and 5 mg of AIBN were dissolved in ethylene glycol dimethyl ether, and then charged into a flask where it was then stirred at a temperature of 75° C. for 3 hours. The reaction solution thus obtained was then reprecipitated from a 10/1 mixture of cyclohexane and ethyl acetate to obtain 0.6 g of a white solid.

50 mg of the polymer thus obtained was dissolved in 5 ml of a buffer having pH 1, buffer having pH 5, buffer having pH 7, buffer having pH 10 and buffer having pH 12, respectively. In this manner, these polymer solutions were measured for its LCST. As a result, these polymer solutions were confirmed to show little or no dependence of the LCST on pH and exhibit an LCST of about 30° C.

EXAMPLE 1-5

Synthesis of trifluoroethyl N-methacroylcarbamate (Scheme b)

Scheme b:

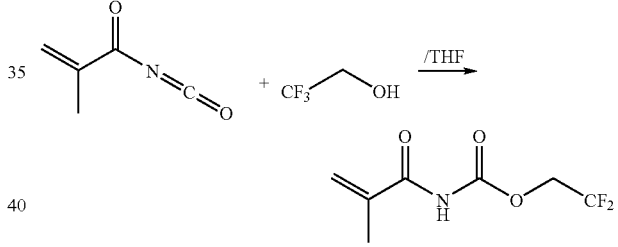

4 ml of methacroyl isocyanate was dissolved in 50 ml of THF in a flask. To the solution was then added dropwise 10 ml of 2,2,2-trifluoroethanol at a temperature of −40° C. in an atmosphere of nitrogen. After the termination of the dropwise addition, the mixture was then stirred at room temperature for 1 hour. The solvent was then distilled off under reduced pressure. The residue was then subjected to silica gel column chromatography with ethyl acetate as a developing solvent. The fraction thus obtained was concentrated, and then recrystallized from ethyl acetate as a solvent to obtain 4.0 g of a white crystal.

NMR analysis gave a strong indication that the product is the desired compound as follows.

NMR analysis: δ2.00 (s, 3H), δ4.52 (qr, 3H), δ5.65 (s, 1H), δ5.96 (s, 1H), δ8.68 (s, 1H).

EXAMPLE 1-6

Synthesis and physical properties of trifluoroethyl poly-N-methacroylcarbamate

In an atmosphere of nitrogen gas, 1.0 g of trifluoroethyl N-methacroycarbamate and 10 mg of AIBN were dissolved in ethanol, and then charged into a flask where it was then stirred at a temperature of 75° C. for 3 hours. The polymer thus precipitated was withdrawn by filtration, thoroughly washed with ethanol, and then dried at room temperature under reduced pressure to obtain 520 mg of a white solid.

50 mg of the polymer thus obtained was then dissolved in 5 ml of a 1 N aqueous solution of sodium hydroxide. To the solution thus obtained was then added dropwise a 0.1 N hydrochloric acid. As a result, it was confirmed that the polymer thus obtained is a pH-responsive polymer which repeatedly undergoes dissolution at a pH value of not less than 10.5 and precipitation at a pH value of not more than 10.5.

EXAMPLE 1-7

Synthesis of N-methacroyl-N-methylurea
(Scheme c)

Scheme c:

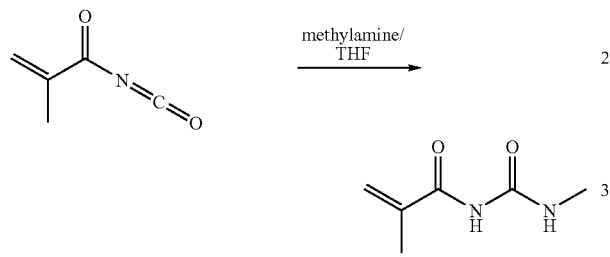

15 ml of methacroyl isocyanate was dissolved in 100 ml of THF in a flask. To the solution was then added dropwise 100 ml of a 2 mol/l THF solution of methylamine at a temperature of −40° C. in an atmosphere of nitrogen. After the termination of the dropwise addition, the mixture was then stirred at room temperature for 1 hour. The solvent was then distilled off under reduced pressure. The residue was then subjected to silica gel column chromatography with ethyl acetate as a developing solvent. The fraction thus obtained was concentrated, and then recrystallized from a 10/1 mixture of ethyl acetate and ethanol as a solvent to obtain 12 g of a white crystal. NMR analysis gave a strong indication that the product is the desired compound.

EXAMPLE 1-8

Synthesis and physical properties of
poly-N-methacroyl-N-methylurea

In an atmosphere of nitrogen gas, 1.0 g of N-methacroyl-N-methylurea and 10 mg of AIBN were dissolved in ethanol, and then charged into a flask where it was then stirred at a temperature of 75° C. for 3 hours. The polymer thus precipitated was withdrawn by filtration, thoroughly washed with ethanol, and then dried at room temperature under reduced pressure to obtain 880 mg of a white solid.

50 mg of the polymer thus obtained was then dissolved in 5 ml of a 1 N aqueous solution of sodium hydroxide. To the solution thus obtained was then added dropwise a 0.1 N hydrochloric acid. As a result, it was confirmed that the polymer thus obtained is a pH-responsive polymer which repeatedly undergoes dissolution at a pH value of not less than 12.1 and precipitation at a pH value of not more than 12.1.

EXAMPLE 1-9

Preparation of Immunoglobulin G-Separating
Adsorptive Material

The separation of immunoglobulin G as target substance was examined using a stimuli-responsive polymer and a protein. As the stimuli-responsive polymer there was used a poly-N-acetyl acrylamide. As the protein there was used Protein A having a specific affinity.

1 g of N-acryloxy succinimide and 20 g of N-acetyl acrylamide were then subjected to polymerization with AIBN as an initiator and ethylene glycol dimethyl ether as a solvent at a temperature of 70° C. for 3 hours. The solid thus precipitated was withdrawn by filtration, thoroughly washed with acetone, and then dried under reduced pressure to obtain 18 g of a copolymer.

The copolymer thus obtained and 5 g of Protein A were dissolved in 500 ml of distilled water at a temperature of 37° C., and then stirred for 12 hours. After the termination of the reaction, to the solution was added 10 ml of ethanol. The temperature of the aqueous solution was adjusted to 15° C. As a result, a copolymer containing Protein A was precipitated. The copolymer thus obtained was withdrawn by filtration, and then thoroughly rinsed with 5° C. distilled water to obtain a stimuli-responsive separating material containing Protein A.

In an atmosphere of nitrogen, 5 g of the stimuli-responsive separating material thus obtained was dissolved in 1,000 ml of a 5% aqueous solution of mouse blood plasma at a temperature of 37° C., and then stirred for 20 minutes. To the solution was then added 20 ml of ethanol. The solution was then cooled to a temperature of 10° C. to cause precipitation. The precipitate thus obtained was then rinsed with saturated brine. The wash water was then analyzed by high-performance liquid chromatography. As a result, it was confirmed that immunoglobulin G having a purity of 92% had been obtained.

In accordance with the first aspect of the present invention, a stimuli-responsive polymer which exhibits an upper critical solution temperature (UCST) or a stimuli-responsive polymer which undergoes reversible dissolution and precipitation depending on the hydrogen ion concentration or an addition of solvent can be obtained.

Further, the use of the above described stimuli-responsive polymer makes it possible to obtain an excellent stimuli-responsive separating material particularly effective for the separation of a target substance which is desirably not to be in a high temperature atmosphere.

EXAMPLE 2-1

Synthesis and physical properties of copolymer of
N-acetyl acrylamide with N-isopropyl acrylamide 1.0 g of N-acetyl acrylamide and 200 mg of N-isopropyl acrylamide were dissolved in 5 ml of ethanol in a three-necked flask. To the solution was then added 5 mg of AIBN. The mixture was then stirred at a temperature of 70° C. for 4 hours. The polymer thus precipitated was washed with ethanol, and then thoroughly dried under reduced pressure to obtain 780 mg of a copolymer (weight-average molecular weight: about 7,000).

25 mg of the copolymer thus obtained was then dissolved in 5 ml of a 15% aqueous solution of ethanol. The copolymer solution was then measured for upper critical solution temperature (UCST). As a result, it was 5° C. The same sample was then measured for lower critical solution temperature (LCST). As a result, it was 83° C.

The upper critical solution temperature (UCST) and the lower critical solution temperature (LCST) were determined as calculated in terms of visible light transmittance.

COMPARATIVE EXAMPLE 2-1

Synthesis and physical properties of poly-N-isopropyl acrylamide (PNIPAM)

In an atmosphere of nitrogen gas, 1.0 g of N-isopropyl acrylamide and 5 mg of AIBN were dissolved in ethylene glycol dimethyl ether, and then charged into a flask where it was then stirred at a temperature of 75° C. for 3 hours. The reaction solution thus obtained was then reprecipitated from a 10/1 mixture of cyclohexane and ethyl acetate to obtain 0.6 g of a white solid.

50 mg of the polymer thus obtained was then dissolved in 5 ml of distilled water. The polymer solution was then measured for lower critical solution temperature (LCST). As a result, it was about 30° C. The aqueous solution was then allowed to stand at a temperature of 1° C. for 1 week. As a result, no polymers were observed precipitated. This demonstrates that the polymer has no upper critical solution temperature (UCST).

In accordance with the second aspect of the present invention, a thermo-responsive polymer having an upper critical solution temperature (UCST) and a lower critical solution temperature (LCST) can be obtained. The thermo-responsive polymer of the present invention is particularly useful for the separation, purification, fixing, calibration or control of substances the working temperature of which can hardly be predetermined (protein such as biological product, enzyme and antibody) or can be effectively used for chemovalve, etc.

EXAMPLE 3-2

Synthesis and physical properties of 1:1 copolymer of N-acetyl acrylamide and N-acetyl methacrylamide In an atmosphere of nitrogen gas, 1.1 g of N-acetyl acrylamide, 1.2 g of N-acetyl methacrylamide and 5 mg of AIBN were dissolved in 10 ml of dimethyl sulfoxide, and then charged in a flask where it was then stirred at a temperature of 75° C. for 3 hours. 200 ml of ethanol and a stirrer were then put in a beaker. To ethanol was then gradually added dropwise the above described reaction solution with vigorous stirring by a magnetic stirrer. The mixture was then stirred for 2 hours. The resulting precipitate was withdrawn by filtration, thoroughly washed with ethanol, and then dried at room temperature under reduced pressure to obtain 2.0 g of a white solid. The white solid had a weight-average molecular weight of about 7,000.

25 mg of the polymer thus obtained was then dissolved in 5 ml of distilled water. The polymer solution was then measured for lower critical solution temperature (LCST). As a result, it was 53° C. Further, the polymer solution showed a transition temperature range as very sharp as 4° C.

Similarly, 25 mg of the same polymer was dissolved in a 0.01 N aqueous solution of caustic soda. The polymer solution was then measured for lower critical solution temperature (LCST). As a result, it was 66° C.

Similarly, 25 mg of the same polymer was dissolved in a 0.1 N aqueous solution of caustic soda. The polymer solution was then measured for lower critical solution temperature (LCST). As a result, the turbid point disappeared.

Similarly, 25 mg of the same polymer was dissolved in a 25% aqueous solution of ethanol. The polymer solution was then measured for lower critical solution temperature (LCST). As a result, the lower critical solution temperature (LCST) disappeared, and an upper critical solution temperature (UCST) was observed at a temperature of 50° C.

The polymer reversibly underwent dissolution and precipitation at this point many times. The transition temperature was measured as calculated in terms of visible light transmittance.

EXAMPLE 3-3

Synthesis and physical properties of 1:4 copolymer of N-acetyl acrylamide and N-acetyl methacrylamide In an atmosphere of nitrogen gas, 1.1 g of N-acetyl acrylamide, 4.8 g of N-acetyl methacrylamide and 5 mg of AIBN were dissolved in 20 ml of dimethyl sulfoxide, and then charged in a flask where it was then stirred at a temperature of 75° C. for 3 hours. 500 ml of ethanol and a stirrer were then put in a beaker. To ethanol was then gradually added dropwise the above described reaction solution with vigorous stirring by a magnetic stirrer. The mixture was then stirred for 2 hours. The resulting precipitate was withdrawn by filtration, thoroughly washed with ethanol, and then dried at room temperature under reduced pressure to obtain 5.5 g of a white solid.

25 mg of the polymer thus obtained was then dissolved in 5 ml of distilled water. The polymer solution was then measured for lower critical solution temperature (LCST). As a result, it was 15° C. Further, the polymer solution showed a transition temperature range as very sharp as 8° C.

Similarly, 25 mg of the same polymer was dissolved in a 0.1 N aqueous solution of caustic soda and a 0.01 N aqueous solution of caustic soda, respectively. The polymer solutions were then measured for lower critical solution temperature (LCST). As a result, the turbid point disappeared.

The polymer reversibly underwent dissolution and precipitation at this point many times. The transition temperature was measured as calculated in terms of visible light transmittance.

EXAMPLE 3-4

Synthesis and physical properties of 2:3 copolymer of N-acetyl acrylamide and N-acetyl methacrylamide In an atmosphere of nitrogen gas, 2.2 g of N-acetyl acrylamide, 2.4 g of N-acetyl methacrylamide and 5 mg of AIBN were dissolved in 20 ml of dimethyl sulfoxide, and then charged in a flask where it was then stirred at a temperature of 75° C. for 3 hours. 400 ml of ethanol and a stirrer were then put in a beaker. To ethanol was then gradually added dropwise the above described reaction solution with vigorous stirring by a magnetic stirrer. The mixture was then stirred for 2 hours. The resulting precipitate was withdrawn by filtration, thoroughly washed with ethanol, and then dried at room temperature under reduced pressure to obtain 4.2 g of a white solid.

25 mg of the polymer thus obtained was then dissolved in 5 ml of distilled water. The polymer solution was then measured for lower critical solution temperature (LCST). As a result, it was 23° C. Further, the polymer solution showed a transition temperature range as very sharp as 5° C.

Similarly, 25 mg of the same polymer was dissolved in 5 ml of a 0.01 N hydrochloric acid. The polymer solution was then measured for lower critical solution temperature (LCST). As a result, it was 25° C. Further, the polymer solution showed a transition temperature range as very sharp as 4° C.

Similarly, 25 mg of the same polymer was dissolved in a 0.01 N aqueous solution of caustic soda. The polymer solution was then measured for lower critical solution temperature (LCST). As a result, it was 68° C.

Similarly, 25 mg of the same polymer was dissolved in a 25% aqueous solution of caustic soda. The polymer solution was then measured for lower critical solution temperature (LCST). As a result, the turbid point disappeared.

Similarly, 25 mg of the same polymer was dissolved in a 30% aqueous solution of ethanol. The polymer solution was then measured for lower critical solution temperature (LCST). As a result, the lower critical solution temperature (LCST) disappeared, and an upper critical solution temperature (UCST) was observed at a temperature of 63° C.

The polymer reversibly underwent dissolution and precipitation at this point many times. The transition temperature was measured as calculated in terms of visible light transmittance.

COMPARATIVE EXAMPLE 3-1

Synthesis and physical properties of poly-N-isopropyl acrylamide (PNIPAM)

In an atmosphere of nitrogen gas, 1.0 g of N-isopropyl acrylamide and 5 mg of AIBN were dissolved in 5 ml of ethylene glycol dimethyl ether, and then charged in a flask where it was then stirred at a temperature of 75° C. for 3 hours. The resulting reaction solution was then recrystallized from a 10/1 mixture of cyclohexane and ethyl acetate to obtain 0.6 g of a white solid.

25 mg of the polymer thus obtained was then dissolved in 5 ml of distilled water, a 0.01 N hydrochloric acid, a 0.01 N aqueous solution of caustic soda and a 0.1 N aqueous solution of caustic soda. The polymer solution was then measured for lower critical solution temperature (LCST). As a result, these polymer solutions showed little or no dependence of the LCST on pH and a lower critical solution temperature (LCST) of about 30° C.

25 mg of the polymer was dissolved in a 20% aqueous solution of ethanol. The polymer solution thus obtained was then measured for turbid point. As a result, the polymer solution showed a lower critical solution temperature (LCST) at a temperature of 19° C. but showed no upper critical solution temperature (UCST).

In accordance with the third aspect of the present invention, a stimuli-responsive polymer which can switch between lower critical solution temperature (LCST) and upper critical solution temperature (UCST) or allow individual occurrence of reversible dissolution and precipitation in a single compound depending on the hydrogen ion concentration can be obtained. The stimuli-responsive polymer of the present invention is particularly useful for the separation, purification, fixing, calibration or control of substances the working temperature of which can hardly be predetermined (protein such as biological product, enzyme and antibody) or can be effectively used for chemovalve, etc.

EXAMPLE 4-1

Synthesis and physical properties of 1:12 copolymer of N-acetyl acrylamide and acrylamide In an atmosphere of nitrogen gas, 100 mg of N-acetyl acrylamide, 1.2 g of acrylamide and 5 mg of AIBN were dissolved in 10 ml of dimethyl sulfoxide, and then charged in a flask where it was then stirred at a temperature of 75° C. for 3 hours. 200 ml of ethanol and a stirrer were then put in a beaker. To ethanol was then gradually added dropwise the above described reaction solution with vigorous stirring by a magnetic stirrer. The mixture was then stirred for 2 hours. The resulting precipitate was withdrawn by filtration, thoroughly washed with ethanol, and then dried at room temperature under reduced pressure to obtain 900 mg of a white solid.

25 mg of the polymer thus obtained was then dissolved in 5 ml of distilled water. The polymer solution was then measured for upper critical solution temperature (UCST). As a result, it was 24° C. The polymer reversibly underwent dissolution and precipitation at this point many times.

EXAMPLE 4-2

Synthesis and physical properties of 1:11 copolymer of N-acetyl acrylamide and acrylamide The procedure of polymerization reaction and purification of Example 1 was followed except that 100 mg of N-acetyl acrylamide, 1.1 g of acrylamide and 5 mg of AIBN were dissolved in 10 ml of dimethyl sulfoxide which was then charged in a flask. As a result, 850 mg of a white solid was obtained.

25 mg of the polymer thus obtained was then dissolved in 5 ml of distilled water. The solution thus obtained was then measured for upper critical solution temperature (UCST). As a result, it was 12° C. The polymer reversibly underwent dissolution and precipitation at this point many times.

EXAMPLE 4-3

Synthesis and physical properties of 1:9 copolymer of N-acetyl acrylamide and acrylamide The procedure of polymerization reaction and purification of Example 1 was followed except that 100 mg of N-acetyl acrylamide, 900 mg of acrylamide and 5 mg of AIBN were dissolved in 10 ml of dimethyl sulfoxide which was then charged in a flask. As a result, 820 mg of a white solid was obtained.

25 mg of the polymer thus obtained was then dissolved in 5 ml of distilled water. The solution thus obtained was then measured for upper critical solution temperature (UCST). As a result, it was 4° C. The polymer reversibly underwent dissolution and precipitation at this point many times.

EXAMPLE 4-4

Synthesis and physical properties of 1:12 copolymer of N-acetyl acrylamide and methacrylamide The procedure of polymerization reaction and purification of Example 1 was followed except that 100 mg of N-acetyl acrylamide, 1.2 g of methacrylamide and 5 mg of AIBN were dissolved in 10 ml of dimethyl sulfoxide which was then charged in a flask. As a result, 880 mg of a white solid was obtained.

25 mg of the polymer thus obtained was then dissolved in 5 ml of distilled water. The solution thus obtained was then measured for upper critical solution temperature (UCST). As a result, it was 21° C. The polymer reversibly underwent dissolution and precipitation at this point many times.

EXAMPLE 4-5

Synthesis and physical properties of 1:11 copolymer of N-acetyl acrylamide and methacrylamide The procedure of polymerization reaction and purification of Example 1 was followed except that 100 mg of N-acetyl acrylamide, 1.1 g of methacrylamide and 5 mg of AIBN were dissolved in 10 ml of dimethyl sulfoxide which was then charged in a flask. As a result, 880 mg of a white solid was obtained.

25 mg of the polymer thus obtained was then dissolved in 5 ml of distilled water. The solution thus obtained was then measured for upper critical solution temperature (UCST). As a result, it was 45° C. The polymer reversibly underwent dissolution and precipitation at this point many times.

EXAMPLE 4-6

Synthesis and physical properties of 1:10 copolymer of N-acetyl acrylamide and methacrylamide The procedure of polymerization reaction and purification of Example 1 was followed except that 100 mg of N-acetyl acrylamide, 1.0 g of methacrylamide and 5 mg of AIBN were dissolved in 10 ml of dimethyl sulfoxide which was then charged in a flask. As a result, 880 mg of a white solid was obtained.

25 mg of the polymer thus obtained was then dissolved in 5 ml of distilled water. The solution thus obtained was then measured for upper critical solution temperature (UCST). As a result, it was 55° C. The polymer reversibly underwent dissolution and precipitation at this point many times.

The measurement of the transition temperature of the samples of Examples 1 to 6 were all effected as calculated in terms of visible light transmittance. Further, all these copolymers repeatedly underwent reversible dissolution and precipitation even in physiological saline, though showing slightly different upper critical solution temperatures (UCST).

EXAMPLE 4-7

Synthesis and separating properties of 1:8 copolymer of N-acetyl methacrylamide and methacrylamide having bithion fixed therein 100 mg of an acrylic acid ester represented by the following general formula d, 100 mg of N-acetyl acrylamide, 1.2 g of methacrylamide and 5 mg of AIBN were dissolved in 10 ml of dimethyl sulfoxide, and then charged in a flask where it was then subjected to polymerization reaction and purification under the same conditions as mentioned above to obtain 760 mg of a white solid.

35° C. of the polymer thus obtained was dissolved in an aqueous solution containing 10 mg of crude avidin (purity: 85% as determined by high-performance liquid chromatography), and then cooled to 5° C. The resulting precipitate was withdrawn by filtration, washed with 5° C. 10% brine, and then filtered. The resulting filtrate was dialyzed through a dialysis tube, and then lyophilized to obtain 2 mg of avidin. The purity of avidin thus obtained was analyzed by high-performance liquid chromatography. As a result, it was 99.8%.

General Formula d

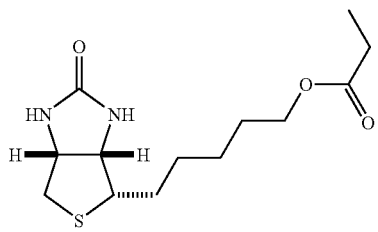

EXAMPLE 4-8

Chemical-Releasing Capsule 100 mg of N-acetyl acrylamide, 1.1 g of methacrylamide, 30 mg of N, N'-methylene bisacrylamide and 5 mg of ammonium persulfate were dissolved in 10 ml of distilled water. The solution was then reacted at a temperature of 10° C. to prepare a gel.

The gel thus prepared was then allowed to swell in 42° C. physiological saline. To the gel was then added an aqueous solution of taxol. In this manner, taxol was allowed to permeate into the gel overnight. Thereafter, the system was cooled to a temperature of 10° C. The gel was withdrawn, thoroughly washed with a low temperature saline, and then dipped in 38° C. physiological saline for 1 hour. The saline was then analyzed by high-performance liquid chromatography. As a result, taxol was confirmed released. Further, the gel was dipped in 10° C. physiological saline. The saline was then analyzed by high-performance liquid chromatography. The release of the chemical was suspended. Thus, no taxol was identified.

In accordance with the fourth aspect of the present invention, a thermo-responsive polymer which exhibits an upper critical solution temperature (UCST) in an aqueous solution, particularly in physiological saline, can be obtained. The thermo-responsive polymer of the present invention is particularly useful for the separation, purification, fixing, calibration or control of substances the working temperature of which can hardly be predetermined (protein such as biological product, enzyme and antibody) or can be effectively used for chemovalve, etc.

While the invention has been described in detail and with reference to specific examples thereof, it will be apparent to one skilled in the art that various changes and modifications can be made therein without departing from the spirit and scope thereof.

What is claimed is:

1. A pH-responsive polymer utilizing keto-enol tautomerism which comprises a polymerizable monomer component which is trifluoroethyl poly-N-methacryoylcarbamate.

* * * * *